United States Patent [19]

Grossman et al.

[11] Patent Number: 5,047,458

[45] Date of Patent: * Sep. 10, 1991

[54] MELAMINE SALTS OF ALKYL ACID PHOSPHATES AS FLAME RETARDANTS FOR POLYMERS

[75] Inventors: Richard F. Grossman, Shelton; Francis W. McKane, Jr., Bridgeport, both of Conn.

[73] Assignee: Synthetic Products Company, Cleveland, Ohio

[*] Notice: The portion of the term of this patent subsequent to May 22, 2007 has been disclaimed.

[21] Appl. No.: 492,945

[22] Filed: Mar. 13, 1990

Related U.S. Application Data

[62] Division of Ser. No. 226,866, Aug. 1, 1988, Pat. No. 4,927,929.

[51] Int. Cl.$^5$ .......................................... C08K 5/3492
[52] U.S. Cl. .................................... 524/100; 544/195; 252/609; 252/400.22
[58] Field of Search ...................... 524/100; 544/195

[56] References Cited

U.S. PATENT DOCUMENTS

| | | | |
|---|---|---|---|
| 2,544,706 | 3/1951 | Malowan | 524/100 |
| 3,887,553 | 6/1975 | Nachbur et al. | 544/195 |
| 4,010,137 | 3/1977 | Brady | 524/100 |
| 4,080,501 | 3/1978 | Leman et al. | 544/195 |
| 4,154,930 | 5/1979 | Halpern | 544/195 |
| 4,201,705 | 5/1980 | Halpern et al. | 524/100 |
| 4,338,245 | 7/1982 | Halpern | 524/100 |
| 4,338,246 | 7/1982 | Halpern | 524/100 |
| 4,342,682 | 8/1982 | Halpern et al. | 523/179 |
| 4,480,093 | 10/1984 | Halpern | 544/195 |

FOREIGN PATENT DOCUMENTS 514819  9/1976  U.S.S.R. ............................ 544/195

*Primary Examiner*—Kriellion S. Morgan
*Attorney, Agent, or Firm*—Wood, Herron & Evans

[57] ABSTRACT

Melamine salts of alkyl acid phosphates are produced by reacting melamine with an alkyl acid phosphate where the alkyl group may be about $C_1$–$C_{20}$. The salts are suitable for use as flame retardants for synthetic polymers.

4 Claims, No Drawings

MELAMINE SALTS OF ALKYL ACID PHOSPHATES AS FLAME RETARDANTS FOR POLYMERS

This is a division of application Ser. No. 07/226,866 filed Aug. 1, 1988, now U.S. Pat. No. 4,927,929.

BACKGROUND OF THE INVENTION

Reaction products of melamine or related species with organic phosphoric acids are known. For example, U.S. Pat. Nos. 4,154,930; 4,201,705; 4,338,245; 4,338,246; 4,342,682 and 4,480,093 are directed to certain amine salts of organic phosphoric acids. The amine salts are useful as flame retardant additives in certain polymeric compositions. In addition to the above mentioned patents, melamine has been reacted with phosphorous pentoxide, phosphoric acid or other phosphorous-containing compounds to produce reaction products that also are useful as flame retardants for synthetic resins as disclosed in U.S. Pat. Nos. 2,544,706; 4,010,137 and 4,080,501. The preparation of melamine flame retardants by techniques disclosed in the above identified patents tends to be hazardous or unattractive. For instance, the reaction of phosphorous oxychloride with pentarythritol, followed by reaction with melamine, is unattractive because it involves generation of six moles of hydrochloric acid per mole of product. In addition, the technique involves the handling of toxic phosphorous oxychloride and highly corrosion-resistant apparatus must be employed. In alternative routes, pentarythritol and melamine are reacted with fuming phosphoric acid, but this technique is equally unattractive. Further improvements are needed in preparation of flame retardants, especially of the melamine-phosphorous containing type without the hazards and disadvantages associated with current techniques.

SUMMARY OF THE INVENTION

This invention is directed to melamine salts of alkyl acid phosphates. Representative alkyl groups in the acid phosphate include methyl, butyl, amyl, octyl, lauryl and stearyl. The salts are produced by reaction of melamine with the corresponding alkyl acid phosphate, preferably in the presence of a diluent.

In one preferred form, amyl acid phosphate is reacted with melamine to produce melamine amyl phosphate. This salt has been found to be dispersible in polymers and is a very effective flame retardant. When melamine amyl phosphate is to be used as a flame retardant for a synthetic resin or elastomer, the reaction can be carried out in the presence of a resin additive such as a plasticizer or elastomeric binder. The hazards and disadvantages associated with prior preparation techniques mentioned in the background of the invention are avoided by the preparation of the simple salts of this invention. The salts of this invention have been found very useful as flame retardants in various polymer systems. When the melamine salts of the alkyl acid phosphates are used as flame retardants; as the alkyl group is increased, flame retardancy decreases. Thus, lauryl melamine phosphate is less effective than octyl in burn time experiments. The methyl salt is an excellent flame retardant, but somewhat difficult to disperse in polymers.

Mono- and dialkyl acid phosphates have been used to react with melamine to prepare mono- and dimelamine alkyl phosphates, and mixtures thereof. In the case of the reaction of melamine with the dialkyl acid phosphate, the monomelamine salt is the reaction product. The dimelamine salt is formed upon reaction of melamine with the monoalkyl acid phosphate. Of course mixtures of such salts will result. In a preferred form for flame retardant use, a one to one molar ratio of melamine to the alkyl acid phosphate has been found to be more effective than mixtures of mono- and dimelamine alkyl phosphates.

DETAILED DESCRIPTION

The melamine alkyl phosphate of this invention is produced by reacting an alkyl acid phosphate such as amyl acid phosphate with melamine to produce stable melamine salts. The novel melamine alkyl phosphates can be produced at room or elevated temperatures by reacting melamine with an alkyl acid phosphate, optionally in an inert media or diluent, and recovering the salt. If the reaction is conducted without a diluent, the heat of reaction is usually sufficient to fuse the product into an intractable lump. Another method of production is to add an alkyl acid phosphate to synthetic resin additives such as silica gel or plasticizer with the addition of powdered melamine to produce a melamine salt of the alkyl acid phosphate.

A. Reaction Product of Amyl Acid Phosphate and Melamine

To a Littleford mixer at room temperature were added 28.4 pounds of amyl acid phosphate and 19 pounds of finely precipitated silica gel (Zeosil 45). After two minutes, 42.5 pounds of powdered melamine was added and, optionally, 10 pounds of DTDP (ditridecyl phthalate) plasticizer were added. After an additional 1 minute of mixing the reaction mixture, coarse white powder was dumped to provide the melamine salt of amyl acid phosphate in the resin additive mixture.

Amyl acid phosphate is an example of a simple alkyl acid phosphate suitable in accordance for use to form the melamine salts of this invention. Amyl acid phosphate can also be provided in a mixture of primary amyl isomers, i.e., $(C_5H_{11})_2HPO_4$ and $C_5H_{11}H_2PO_4$ as a water-white liquid having a density of about 1.07–1.09 and a flash point (COC) of 245° F. Other alkyl acid phosphates may be employed as will be understood to a person of ordinary skill in the art, typically where the alkyl group is $C_1$ to about $C_{20}$. The salts of melamine may either be mono- or polymelamine salts of the alkyl acid phosphates, depending upon the availability of salt forming hydrogen and amino groups of melamine, and the stoichiometry of the reaction.

B. Use of Melamine Amyl Phosphate as a Flame Retardant in Polymers

EXAMPLE 1

Ethylene propylene diene monomer (EPDM) formulation

The base formula for this EPDM polymer composition containing the melamine amyl phosphate component was formulated as follows:

| | |
|---|---|
| Epsyn 2308 | 100 |
| Alumina trihydrate | X1 |
| Basic Mag carbonate | X2 |
| Melamine amyl phosphate | X3 |
| C-473 | 2.5% of X1 + 22 + X3 |
| B-5405 | 2 |
| Zinc oxide | 5 |

| | |
|---|---|
| -continued | |
| 2280 oil | 5% of X1 + X2 + X3 |
| AgeRite MA | 1 |
| Vulcup 40KE | 6 |

Epsyn 2308 is a terpolymer of 75 to 80 mol percent ethylene, 17 to 22 propylene, the remainder ENB (ethylidene norbornene) third monomer, having a Mooney viscosity of circa 30 at 100° C., supplied by Copolymer Rubber & Chemical Corp. Alumina trihydrate (ATH) is hydrous aluminum oxide (Hydral 710) supplied by Alcoa. Basic magnesium (mag) carbonate is supplied by Morton Thiokol. C-473 is a mixture of 60% paraffin wax and 40% vinyl tris-(beta-methoxyethoxy)-silane, supplied by Union Carbide under the trade name A-172. B-5405 is a mixture of 25% diatomaceous earth and 75% trimethylolpropane trimethacrylate, supplied by Sartomer Co. under the trade name SR-350. 2280 oil is a paraffinic oil of Type 104B per ASTM D 2226 supplied by Sun Oil as Sunpar 2280. AgeRite MA is a low polymer of 1,2-dihydro-2,2,4-trimethyl quinoline, a well known antioxidant supplied by R. T. Vanderbilt. Vulcup 40KE consists of 60% calcined clay, 40% bis(t-butylperoxy)di-isopropylbenzene, supplied by Hercules Inc.

By employing the above formula and holding basic magnesium carbonate and melamine amyl phosphate at 0, aluminum trihydrate was varied from about 150 to 250 parts. Below 200 parts, the formula was slow burning under Bunsen burner flame conditions per ASTM D568. At 200 parts, the compound becomes self-extinguishing under similar conditions and at 250 parts it became non-burning. By holding aluminum trihydrate and melamine amyl phosphate at 0 parts in the above formula, basic magnesium carbonate was similarly varied and, the composition in this event was self-extinguishing at 185 parts and non-burning at 225 parts. By holding both aluminum trihydrate and basic magnesium carbonate at 0, the formula becomes self-extinguishing at 35 parts of melamine amyl phosphate and non-burning at 75 parts. With alumina trihydrate at 175 parts and basic magnesium carbonate at 0, the composition became self-extinguishing at 15 parts of melamine amyl phosphate and non-burning at 25 parts. At 175 parts of alumina trihydrate and 15 parts of melamine amyl phosphate, tensile strength was about 1650 and ultimate elongation of 195. Decreasing alumina trihydrate to 150 parts, the composition becomes self-extinguishing with melamine amyl phosphate at 15 parts and becomes non-burning with melamine salt at 25 parts. Similarly, with alumina trihydrate at 0 parts and basic magnesium carbonate at 100 parts, the composition becomes self-extinguishing with melamine amyl phosphate at 12.5 parts and non-burning at 25 parts. This latter composition also provided improved physical properties with tensile at 1780 and elongation at 350.

EXAMPLE 2

Ethylene vinyl acetate (EVA) composition

The base formula for this polymer composition containing the melamine amyl phosphate component was formulated as follows:

| | |
|---|---|
| Vynathene EY-903 | 100 |
| Alumina trihydrate | X1 |
| Basic Mag carbonate | X2 |
| Melamine amyl phosphate | X3 |
| C-473 | 2.5% of X1 + X2 + X3 |
| B-5405 | 3 |
| Zinc stearate | 2 |
| Santonox R | 1 |
| DiCup 40KE | 8 |

Vynathene EY-903 is a copolymer of circa 60% ethylene, 40% vinyl acetate supplied by USI. Santonox R is an antioxidant, 4,4'-thiobis(6-t-butyl-metacresol) from Monsanto. DiCup 40 KE consists of 60% calcined clay, 40% dicumyl peroxide, from Hercules. Other materials are identified in EXAMPLE 1.

In a manner similar to EXAMPLE 1 for EPDM, the alumina trihydrate, basic magnesium carbonate and melamine amyl phosphate components were varied over similar parts by weight to demonstrate the self-extinguishing and non-burning characteristics of compositions containing the melamine amyl phosphate. Thus, it has been adequately demonstrated that the melamine amyl phosphate salt of this invention satisfactorily contributes as a flame retardant in hydrocarbon polymer compositions. Other polymers such as PVC may be rendered flame retardant with the melamine alkyl phosphate of this invention.

In view of the above description, other modifications will be apparent to a person of ordinary skill in the art and such are within the scope of this invention.

What is claimed is:

1. A flame retardant composition for a synthetic polymer comprising a melamine salt of an alkyl acid phosphate where the alkyl group is $C_1$ to about $C_{20}$.

2. The flame retardant composition of claim 1 wherein said salt is the monomelamine salt.

3. The flame retardant composition of claim 1 wherein said salt is melamine amyl phosphate.

4. The composition of claim 1 wherein said polymer is derived from the group of monomeric ethylene, propylene, and copolymers thereof.

* * * * *